United States Patent [19]

Groh et al.

[11] Patent Number: 4,642,363

[45] Date of Patent: Feb. 10, 1987

[54] METHOD OF PREPARING TRIALKYL ORGANO-OXYSILANES

[75] Inventors: Reiner Groh, Steyerberg; Hans-Joachim Kötzsch; Hans-Günther Srebny, both of Rheinfelden; Hans-Joachim Vahlensieck, Wehr, all of Fed. Rep. of Germany

[73] Assignee: Dynamit Nobel AG, Cologne, Fed. Rep. of Germany

[21] Appl. No.: 769,943

[22] Filed: Aug. 27, 1985

[30] Foreign Application Priority Data

Aug. 30, 1984 [DE] Fed. Rep. of Germany ....... 3431839

[51] Int. Cl.$^4$ ................................................ C07F 7/18
[52] U.S. Cl. .................................................... 556/471
[58] Field of Search ......................................... 556/471

[56] References Cited

U.S. PATENT DOCUMENTS

| 2,553,895 | 5/1951 | Clark | 556/471 |
| 3,567,756 | 3/1971 | Rothe | 556/471 |
| 3,801,618 | 4/1974 | Walker | 556/471 |
| 3,985,781 | 10/1976 | Kötzsch et al. | 556/471 X |
| 4,039,567 | 8/1977 | Kötzsch et al. | 556/471 X |
| 4,228,092 | 10/1980 | Kötzsch et al. | 556/471 X |
| 4,506,087 | 3/1985 | Fischer et al. | 556/471 |

*Primary Examiner*—Paul F. Shaver
*Attorney, Agent, or Firm*—Felfe & Lynch

[57] ABSTRACT

A method for the continuous or batch preparation of trialkyl organo-oxysilanes by reaction of organic hydroxy compounds with trialkyl halogen silanes in the absence of acid-binding substances is disclosed. The organic hydroxy compound is added directly to the trialkoxy halogen silane in an amount which corresponds to no more than the stoichiometrically necessary amount. The trialkyl halogen silane, or the resultant mixture is always at the boiling temperature or above the boiling temperature in the gaseous state. The reaction mixture is subjected, no later than toward the end of the reaction, to a column distillation in which the column temperature is held such that the reaction is carried to the end within the column. In continuous operation, the trialkyl halogen silane is introduced in gaseous form into the bottom of a column and either kept under reflux or introduced into a reactor into which corresponding stoichiometric amounts of organic hydroxy compound are simultaneously introduced. In the column, either a raw product or freshly introduced organic hydroxy compound in liquid form flows against the gaseous trialkyl halogen silane, and the desired trailkyl organo-oxysilane collects at ebullition on the floor of the column and is continuously removed.

5 Claims, 1 Drawing Figure

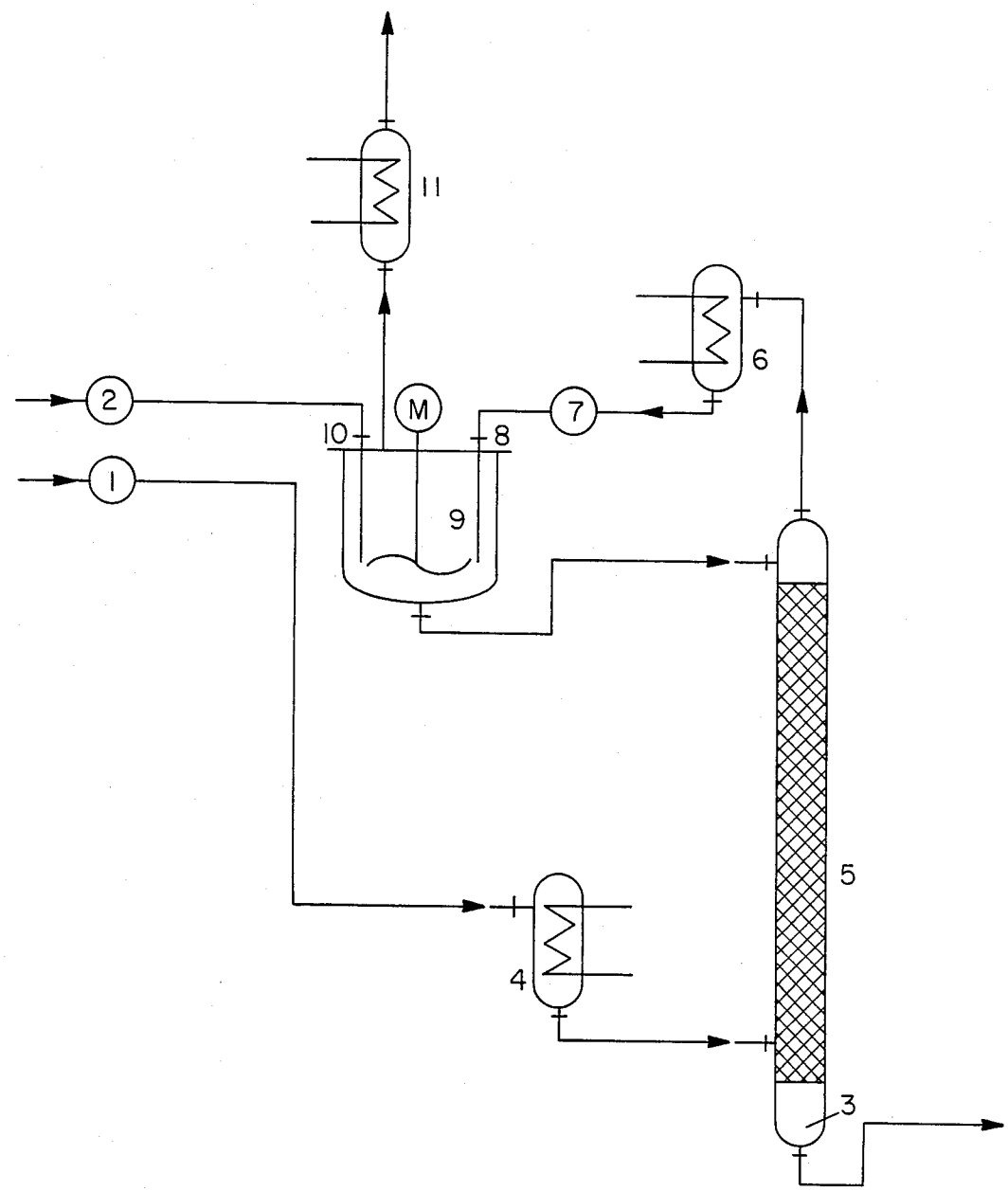

METHOD OF PREPARING TRIALKYL ORGANO-OXYSILANES

BACKGROUND OF THE INVENTION

The subject matter of the present invention is a method of preparing trialkyl organo-oxysilanes of Formula I $R_3SiOR'$ by the esterification of trialkyl halogen silanes of Formula II $R_3SiHal$ with organic hydroxy compounds of formula III $R'OH$ with the release of gaseous hydrogen chloride.

In the above formulas, R represents identical or different aliphatic alkyl moieties of 1 to 4 carbon atoms, which can be either saturated or unsaturated and/or branched. R' represents a saturated or unsaturated aliphatic alkyl or acyl moiety, which also can be branched and/or cyclic and/or can contain ether oxygen bridges or ester groups, or can be aromatically substituted, or R' can represent an aromatic aryl or aroyl moiety which can bear hydrocarbon and/or halogen substituents and/or nitro substituents.

It is known that trialkylchlorosilanes react poorly with organic hydroxy compounds (cf. J. Org. Chem. 23 (1958), 50 to 58). Especially the complete reaction encounters the difficulty that the trialkyl organo-oxysilane that develops reacts with the nascent halogen hydride to form the starting substances, so that a certain amount of trialkyl halogen silane and hydroxy educt always remains in the reaction mixture. To remedy this disadvantage it has been proposed that the esterification reaction of trialkyl chlorosilanes with alcohols be performed in the presence of acid acceptors in order to bring the reaction to completion (J. Chem. Soc. 1956, 1536 to 1539, or J. Org. Chem. 23 (1958), 50 to 58). These known methods however, have the disadvantage of the inevitable production of ammonium chlorides, which reduce the yield on account of their adsorptive properties; furthermore, the separation of the ammonium chlorides from the reaction mixture involves a great deal of difficulty.

The procedure described in German Federal OS No. 30 00 782, of limiting the above-described re-formation of trimethylchlorosilanes by use of an excess of alcohol, leads to secondary reactions whereby disiloxane and alkyl or acyl chloride are formed, and hence it leads to losses of yield. This latter method is usable for tetrachlorosilanes and trichlorosilanes and, under certain circumstances for dichlorosilanes within narrowly defined conditions, but it is not suited for the esterification of trialkyl chlorosilanes. This is because in this case large percentages of alkyl and acyl chlorides and disiloxanes are formed, while trialkylsilyl esters are obtained in only a low yield.

The problem therefore existed of finding a generally usable method for the esterification of trialkyl halogen silanes with organic hydroxy compounds, which will not have the disadvantages described above, and will give yields permitting economical technical utilization.

SUMMARY OF THE INVENTION

To solve this problem, a method has now been found for the preparation of trialkyl organo-oxysilanes of the formula $R_3SiOR$ ($R=C_{1-4}$ alkyl) by the reaction of trialkyl halogen silanes of the formula $R_3SiHal$ (Hal=Cl or Br) with organic hydroxy compounds of the formula $R'OH$ (R'=alkyl, acyl, aryl or aroyl) and removal of the hydrogen chloride forming in the reaction, which is characterized by the fact that the organic hydroxy compound is added, in amounts up to and including the stoichiometric amount necessary for the reaction, to the trialkyl halogen silane maintained at or above the boiling temperature, the reaction mixture being kept under the conditions of a column distillation, at least toward the end of the reaction if not sooner, the hydrogen chloride that forms, plus any excess trialkyl halogen silane, being distilled off and the trialkyl organo-oxysilane being then isolated.

In the use of this procedure in accordance with the invention, especially if it is performed continuously, the desired trialkyl silane esters of formula I are regularly obtained in an approximately quantitative yield. According to the invention, a stoichiometric excess of the educt R'OH is prevented in the column in every phase of the reaction and processing.

The procedure of the invention can be performed continuously or discontinuously. In either case the organic hydroxy compound is fed to the trialkyl halogen silane or to the reaction mixture containing the trialkyl halogen silane, such that it does not come in contact with the hydrogen chloride forming in the gaseous phase.

The hydroxy compound reacts with the trialkyl halogen silane at a temperature that is at or above the boiling temperature of the trialkyl halogen silane or of the developing reaction mixture. The temperature adjustment is made, as a rule, at standard pressure, but a pressure below standard can also be applied.

It is furthermore essential to the process that at least the end of the reaction be performed under the conditions of a column distillation. In this case the reaction mixture is both in gaseous and in liquid form. The internal temperature of the column must be adjusted such that these conditions are sustained at least as long as the halogen hydride is still forming, so that only the latter, and any excess trialkyl halogen silane, will be drawn off at the top in gaseous form.

In the continuous process, the temperature of the column is maintained such that the desired trialkyl organo-oxysilane in the bottom of the column can be withdrawn at ebullition, while in the batch process, after the separation of the hydrogen chloride and any excess trialkyl halogen silane, plus any solvent that has been used, the trialkyl organo-oxysilane is preferably likewise distilled out through the column.

In the batch process, the organic hydroxy compound, which is also referred to hereinafter as "educt III", is delivered in liquid form directly into the boiling liquid reaction phase containing the trialkyl halogen silane without coming in contact with the gaseous phase of the reactor. This gaseous phase contains the developing hydrogen chloride in gaseous form.

In the continuous process according to the invention, the reaction mixture is delivered from the reactor in a steady stream to the middle inlet of a continuously operating column into which a stoichiometric amount of trialkyl halogen silane, corresponding to the trialkyl silane ester being produced, is continuously fed in gaseous form. The top product of this column consists of the trialkyl halogen silane, which is condensed and fed into the reactor, while educt III is proportioned constantly and continuously into the reactor while maintaining the molar ratios of the two starting compounds in accordance with the invention. The halogen hydride that forms leaves the apparatus through a gas cooler on the reactor. The trialkyl organo-oxysilane product is continuously withdrawn from the bottom of the column at ebullition, free of hydrogen chloride.

In the continuous process according to the invention, however, it is possible to do entirely without the separate reactor by feeding the column referred to in the previous paragraph with educt III instead of the reaction mixture, with total refluxing, thus shifting the reaction, while maintaining its full continuity, to the middle to upper part of the column, while the developing hydrogen chloride is removed through a top condenser.

The process in accordance with the invention can also be performed in the presence of inert solvents if compounds of higher boiling point, especially higher-boiling trialkyl halogen silanes, are used as starting products. Solvents are preferred which have lower boiling points than the trialkyl silane esters of formula I.

An apparatus suitable for the practice of the method of the invention is a normal stirrer reactor with a reflux condenser and a hydrogen chloride exhaust permitting the reuse of the hydrogen chloride, and with a feed tube immersed in the liquid reaction phase, through which the organic hydroxy compound is fed.

Instead of being equipped with a reflux condenser, the stirrer reactor can be equipped with a column through the top of which halogen hydride is first withdrawn in gaseous form, and which, especially in the case of batch operation, is first operated with refluxing while the organic compound is being fed in, and finally serves for the purification of the silane esters of formula I prepared according to the invention.

One embodiment of the process of the invention is a continuous process performed in a reactor with a column attached to it. In this embodiment the organic hydroxy compound is fed in liquid form into the liquid, boiling reaction phase of a reactor, without coming in contact with the gaseous phase. The stoichiometric amount of trialkyl halogen silane corresponding to the desired silane ester I is fed in gas form into the bottom part of a column, condensed at the top of the column, and fed into the reactor. The reaction mixture forming in the reactor is continuously fed into the upper part of the column in which it reacts completely with countercurrent trialkyl halogen silane. The desired trialkyl organo-oxysilane, which is free of halogen hydride and the starting compounds, flows into the bottom of the column which is maintained at the boiling temperature of the trialkyl organo-oxysilane. The pure product is withdrawn continuously from the bottom of the column.

The varying features of novelty which characterize the invention are pointed out with particularity in the claims annexed to and forming a part of this specification. For a better understanding of the invention, its operating advantages and specific objects obtained by its use, reference should be had to the accompanying drawings and descriptive matter in which there is illustrated and described a preferred embodiment of the invention.

BRIEF DESCRIPTION OF THE DRAWING

The FIGURE is a schematic generally depicting the process of the invention.

DESCRIPTION OF PREFERRED EMBODIMENT

Generally referring to the Figure, the starting substances II (R$_3$SiHal) and III (R'OH) are continuously fed in the stoichiometric ratio through the proportioning flow meters 1 and 2 respectively. The input trialkyl halogen silane is evaporated in the heat exchanger 4 and delivered into the bottom part of column 5, condensed in heat exchanger 6 after leaving the column, and introduced in liquid form through the flow meter 7 and a submerged tube 8 into the reactor 9. The organic hydroxy compound (III) is proportioned into the reactor by means of the controlled flow meter 2 through a second submerged tube 10. The halogen hydride that is yielded in the reaction escapes through the heat exchanger 11. From the reactor 9 flows a raw product which may still contain halogen hydride and starting products II and III that have not yet completely reacted. This is delivered to the upper part of the column 5. The trialkyl organo-oxysilane is continuously withdrawn from the bottom 3 of the column.

The reaction temperatures can be freely selected within a broad range. The optimum temperature range is dependent upon the starting substance, and is between 40° C. and 200° C.

In the continuous method of conducting the process, the starting products are fed in a stoichiometric ratio. By selecting the start-up conditions, the ratio of educts II and III in the reactor 9 can be varied in virtually any desired manner. According to the invention the trialkyl halogen silane II (herein also referred to as educt II) is used at least in stoichiometric ratio. If, for example, the raw product is placed in the reactor with a certain excess of halogen silane, this excess halogen silane will be returned positively from column 5 back into the reactor 9. The flow meter 7 in this case shows higher values than flow meter 1. Instead of the excess halogen silane, or in addition thereto, a suitable inert solvent can be included additionally in the reactor upon start-up. In this case again a corresponding circulation will begin between reactor 9 and column 5. It is assumed also in this case that the boiling point of the solvent is lower than the column temperature at the bottom.

These different possibilities for the practice of the method of the invention permit the adjustment, in a simple manner, of optimum conditions of reaction and purification for the various products of general formula I which can be prepared in accordance with the invention.

The alkyl moiety R in general formula I for the trialkyl halogen silane can be either a saturated or an unsaturated aliphatic moiety. Branching is also possible. It is preferably unsubstituted and contains up to 4 carbon atoms. The three moieties R can be the same or different.

Suitable starting substances of general formula II for the method of the invention are accordingly trimethylchlorosilane, ethyldimethylchlorosilane, n-propyldimethylchlorosilane, n-butyldimethylchlorosilane, isobutyldimethylchlorosilane, sec.-butyldimethylchlorosilane, tert.-butyldimethylchlorosilane, vinyldimethylchlorosilane, allyldimethylchlorosilane, triethylchlorosilane, etc. In the case of the organic hydroxy compounds used as educts of formula III, the alkyl group or acyl group R' can also be saturated or unsaturated. Branching or substitution by aromatic moieties are likewise possible; cyclic alkyl moieties are also possible. The number of the carbon atoms in these alkyl moieties can amount to as many as 18. The alkyl moiety can also contain ether-oxygen bridges or ester groups.

If the moiety R' represents an aromatic moiety, it can also be substituted by low alkyl moietities or halogen or nitro groups.

Suitable starting products of general formula III are accordingly, for example, methanol, ethanol, n-propanol, isopropanol, allyl alcohol, n-, iso- and secondary butanol, cyclohexanol, 2-ethylhexanol, the pentanols, the octanols, the nonanols, decanol, dodecanol, cetyl alcohol, octadecyl alcohol, oleanol, iso-borneol, menthol, ethylene glycol monomethyl ether, 2-methoxypropanol, 1-methoxypropanol-(2), benzyl alcohol, benzhydrol, phenol, o-, m- and p-cresol, the xylenols, o-, m- and p-chloro-, bromo- and iodophenol, 4-chloro-3,5-xylenol, 2,4,6-trichloro-3,5-xylenol, nonylphenol, alpha and beta naphthaol, 9-anthranol, formic acid, acetic acid, propionic acid, isobutyric acid, methacrylic acid, vinylacetic acid, lactic acid ethyl ester, glycolic acid butyl ester, acetic acid ethyl ester, benzoic acid, o-chlorobenzoic acid, toluoic acid, xyloic acid, naphthoic acid, etc.

Examples of suitable inert solvents are pentanes, hexanes, n-heptane, ixooctane, cyclohexane, methylcyclohexane, benzene, toluene, xylene, durene, tetralin, decalin, transdichloroethylene, chloroform, carbon tetrachloride, trichloroethylene, perchloroethylene, trifluorotrichloroethane, the trichloroethanes, chiefly 1,1,1-trichloroethane, etc.

Products to be made by the method of the invention are, for example, trimethylmethoxy-, -ethoxy-, -n- and iso-propoxy-, -n-, -iso- and sec-butoxy-, -allyloxy-, and -iso-pentyl-oxy, -hexoxy-, -octooxy, cetyloxy- dodecyloxy-, -phenoxy-, -o-, -m- and -p-cresyloxy, -pentafluorophenoxy-, acetoxy- and -benzooxysilane, trimethyl-2-methoxyisopropoxysilane, omega-methoxyethyleneglycoloxytrimethylsilane, ethyldimethylethoxysilane, propyldimethylethoxysilane, vinyldimethylmethoxy-, -ethoxy- and -acetoxysilane, isobutyl- and tert.-butyldimethylmethoxy-, -ethoxy-, -allyloxy- and -acetoxysilane, triethylacetoxy-, -ethoxy- and -n-propoxysilane, etc.

The trialkyl organoxy-silanes of general formula I prepared in accordance with the invention serve as carriers of the trialkylsilyl group under mild conditions. In addition to their importance as silylating agents, this class of substances has lately aroused considerable interest as reagents for the selective and partial esterification of a variety of halides of metals such as titanium, zirconium, vanadium, niobium etc., whose esters and partial esters are gaining portance as catalysts, for example in stereo-selective organic synthesis and in the preparation of polyolefins and tactic polymers, for example.

The following examples will explain the invention but not limit its scope.

EXAMPLES

Example 1

Preparation of trimethylethoxysilane

In a 4-liter stirring reactor heated by a thermostat and equipped with an internal thermometer, surmounted by a packed column with nitrogen gas flooding and a hydrogen chloride exhaust and having a dropping funnel with its bottom submerged in the liquid reaction phase, 2170 g (20 mol) of trimethylchlorosilane was placed and heated to ebullition (b.p. 57.2° C.). The top of the column was set for refluxing. Over a period of about 170 minutes, 700 g (about 16 mol) of anhydrous ethanol was then fed in a manner similar to Example 1, while the boiling temperature steadily increased to 65° C. As boiling continued, 68° C. became constant. Then the top of the column was put into operation and the mixture was distilled. In all, 1.92 kg (approx. 96% yield) of pure trimethylethoxysilane was isolated. B.p. 75° C., D.4/20 0.758.

Example 2

Continuous preparation of trimethylethoxysilane

In a stem-heated 40-liter reactor, equipped with stirrer, two submerged tubes and a gas condenser, 10 liters of trimethylchlorosilane were placed and brought to a boil. The reactor is a component of a continuous system as shown in FIG. 1.

Through the controlled flow meter 1, 112 moles per hour of trimethylchlorosilane in gaseous form was fed into the bottom part of the column 5 (the column has a diameter of 150 mm and is filled with 10-mm porcelain saddles). Boiling pure product was put into the base of the column at the beginning. The trimethylchlorosilane distilling out at the top was condensed and fed through the submerged tube 8 into the reactor 9. At the same time, 112 moles per hour of ethanol were fed through the controlled flow meter 2 and the submerged tube 10. The reactor temperature rose to about 58° C. The raw product flowing from the reactor was put into the upper part of the column. About 12 kg per hour of trimethylethoxysilane was withdrawn continuously from the bottom of the column.

Example 3

Continuous preparation of trimethyl-n-butoxysilane

In a manner similar to Example 2, 80 moles each of trimethylchlorosilane and n-butane were used. The reactor temperature rose to about 88° C. In about 225 hours of operation about 2700 kg of trimethyl-n-butoxysilane was produced in this manner in a virtually quantitative yield. B.p. 124° C.; D.4/20 0.7772.

Example 4

Continuous preparation of vinyldimethylethoxysilane

In a manner similar to Example 2, 6 liters of trans-dichloroethylene and 4 liters of vinyldimethylchlorosilane were placed in the reactor at ebullition, and then the process was performed with 80 moles per hour each of vinyldimethylchlorosilane and ethanol. The reactor temperature went to about 71° C. About 10 kg of vinyldimethylethoxysilane was obtained per hour. B.p. 100° C., D.4/20 0.7889.

Example 5

Continuous preparation of trimethylacetoxysilane

The procedure of Example 2 was performed with 100 mol each of trimethylchlorosilane and anhydrous liquid acetic acid. The reactor temperature went to approximately 83° C. In about 90 hours of operation, about 1.3 metric tons of trimethylacetoxysilane were produced. B.p. 103.5° C., D.4/20 0.8914.

Example 6

Continuous preparation of trimethylmethoxyisopropoxysilane

As in Example 2, 8 liters of trichloroethylene and 2 liters of trimethylchlorosilane were placed in the reactor 8, and then the process was performed with 70 moles per hour each of trimethylchlorosilane a 2-methoxy-iso-propanol. The reactor temperature went to about 67° C. About 11 kg/h of trimethyl-2-methoxyisopropoxysilane was obtained. B.p. 133° C., D.4/20 0.8332.

Example 7

Continuous preparation of trimethylcresyloxysilane

The procedure of Example 2 was perfomred with 40 moles each of trimethylchlorosilane and p-cresol. The reactor temperature went to about 122° C. About 7.2 kg/h of trimethyl-p-cresyloxysilane was produced. B.p. 198° C., D.4/20 0.9183.

Example 8

Preparation of trimethylpentafluorophenoxysilane

In a manner similar to Example 1, 2.5 mol of boiling trimethylchlorosilane was placed without solvent in a 2-liter reactor which contained, instead of the packed column, a reflux condenser (nitrogen gas flooded, with hydrogen chloride exhaust), and about 2 mol (370 g) of pentafluorophenol (m.p. 39° C.) in molten form was fed into it over a period of 30 minutes. The reactor temperature then rose to about 124° C. As boiling continued the temperature rose to about 160° C. in 90 minutes. Then a distillation was performed at about 300 mbar and 118° C. The yield of trimethylpentafluorophenoxysilane was virtually quantitative.

Example 9

Preparation of triethylacetoxysilane

In a manner similar to Example 1, 1510 g (about 20 mol) of triethylchlorosilane and 500 ml of heptane were placed at ebullition in the reactor and over a period of 80 minutes 600 g (10 mol) of anhydrous liquid acetic acid was fed into it, the reactor temperature rising to about 130° C. As boiling continued the boiling temperature increased to about 160° C. Distillation yielded 1630 g (93.5% yield) of triethylacetoxysilane, b.p. 174° C., D.4/20 0.895.

Example 10

Continuous preparation of trimethylisopropoxysilane in a reactor column

In an enameled column of 27 trays, 150 mm diameter, packed with 10-mm porcelain saddles, and having a 2-square meter reflux condenser followed by a 5-square meter gas condenser ($-44°$ C. for exhausting HCl) boiling pure product was first placed in the steam-heated bottom. Then, through an introduction tube 1.5 m above the bottom, 112 moles per hour of trimethylchlorosilane in gaseous form were fed into the column (through a controlled flow-meter), and finally, after the trimethylchlorosilane boiling point of 57° C. was reached, 112 mol/h of liquid isopropanol was measured into the column through a second introduction tube 0.5 m below the reflux head by means of a proportioning pump. The top temperature went to about 55° to 56° C., the bottom temperature to about 87° C. Through the gas condenser about 112 kmol of HCl per hour was exhausted through the gas condenser. About 14.8 kg per hour of trimethylisopropoxysilane was removed continuously from the bottom of the column.

It will be understood that the specification and examples are illustrative but not limitative of the present invention and that other embodiments within the spirit and scope of the invention will suggest themselves to those skilled in the art.

We claim:

1. A process for the preparation of trialkylorganosilanes of the formula $R_3SiOR'$, wherein R is an alkyl radical of 1 to 4 carbon atoms, R' is an alkyl, acyl, aryl or aroyl radical and hal is chlorine or bromine comprising reacting a trialkylhalogensilane of the formula $R_3Si$-hal with an organic hydroxy compound of the formula R'OH, and removing hydrogen chloride formed in the reaction, wherein the organic hydroxy compound is added directly to the trialkylhalogensilane, which is maintained at its boiling temperature and in such amounts, that the molar ratio of hydroxy compound to trialkylhalogensilane does not exceed 1, said organic hydroxy compound being added such that it does not come into contact with the hydrogen chloride formed in the gas phase, subsequently maintaining the reaction mixture under column distillation conditions; distilling off any additionally formed hydrogen chloride and any excess of trialkylhalogensilane; and isolating the trialkylorganosilane.

2. The method of claim 1, wherein the additionally formed hydrogen chloride and excess trialkylhalogensilane are distilled off simultaneously.

3. The process of claim 1 conducted distinuously further comprising introducing the organic hydroxy compound in liquid form below the surface of the trialkylhalogensilane which is maintained at its boiling temperature; maintaining the reaction mixture at the boiling point when said introduction has been completed, distilling off crude product obtained over a column in such a manner that said reaction is completed in said column; and distilling pure trialkylorganoxysilane off over the stillhead of the column.

4. The process of claim 1 conducted in a continuous manner further comprising maintaining the trialkylhalogensilane at its boiling point in a reactor; introducing trialkylhalogensilane and organic hydroxy compound in liquid form below the surface of the trialkylhalogensilane; continuously feeding the reaction mixture formed in the reactor vessel to an upper part of a column, which is maintained at such a temperature that the trialkylorganoxysilane collects at the boiling temperature in the sump of the column and is drawn off continuously, while unreacted trialkylhalogensilane and trialkylhalogensilane, freshly supplied over a lower part of the column, are distilled off over the stillhead and, after condensation, are returned to the reactor.

5. The process of claim 1 conducted in a continuous manner, wherein the organic hydroxy compound is added in liquid form to the head or the upper part of a column adjusted to reflux, the corresponding stoichiometric amount of trialkylhalogensilane is added to the lower part of the column, the hydrogen chloride formed is drawn off over a condenser attached to the head of the column and the hydrogen chloride-free, trialkylorganoxysilane is taken off at the lower end of the column.

* * * * *